United States Patent [19]

Collins et al.

[11] 3,962,295
[45] June 8, 1976

[54] NOVEL DIORGANOTIN DERIVATIVES OF α, ω-DIMERCAPTANS AND METHOD FOR PREPARING SAME

[76] Inventors: John Desmond Collins, 14 Windsor Road, Albrighton, Shropshire; Harold Coates, 60 Ounsdale Road, Wombourn, Staffordshire; Iftikhar Hussain Siddiqui, 8 Wadhurst Road, Edgbaston, Birmingham, 13, Warwickshire, all of England

[22] Filed: Dec. 17, 1974

[21] Appl. No.: 533,535

Related U.S. Application Data

[63] Continuation-in-part of Ser. No. 359,176, May 10, 1973, abandoned.

[30] Foreign Application Priority Data

May 10, 1972 United Kingdom............... 21826/72

[52] U.S. Cl. ........................................... 260/429.7
[51] Int. Cl.² ......................................... C07F 7/22
[58] Field of Search ............................... 260/429.7

[56] References Cited
UNITED STATES PATENTS

| | | |
|---|---|---|
| 3,409,651 | 11/1968 | Horrocks ........................ 260/429.7 |
| 3,409,652 | 11/1968 | Horrocks ........................ 260/429.7 |
| 3,525,761 | 8/1970 | Seki et al. ....................... 260/429.7 |
| 3,534,121 | 10/1970 | Eggensperger et al. ......... 260/429.7 |

*Primary Examiner*—Helen M. S. Sneed

[57] ABSTRACT

Organothiotin compounds with low tin content suitable as stabilizers for halogen containing resins e.g. polyvinyl chloride, are of formula

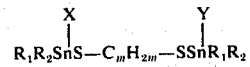

wherein $R_1$ and $R_2$ are individually selected from the group consisting of alkyl radicals containing between 1 and 20 carbon atoms, cycloalkyl and phenyl radicals, $m$ is an integer between 1 and 8, inclusive, and X and Y and individually selected from the group of radicals exhibiting the formulae

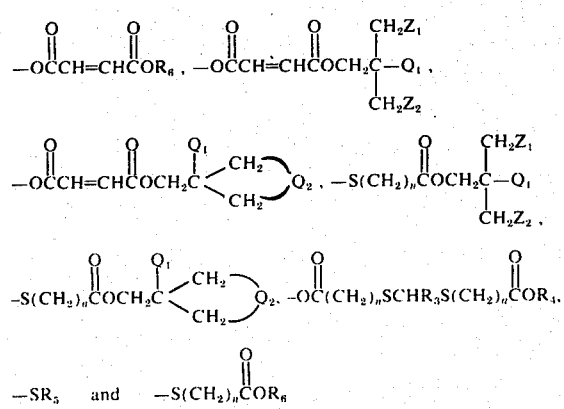

wherein $Q_1$ represents a hydrogen atom, an alkyl radical containing between 1 and 6 carbon atoms, inclusive, or the radical $CH_2Z_3$, wherein $Z_1$, $Z_2$ and $Z_3$ are individually selected from the group of radicals exhibiting the formulae

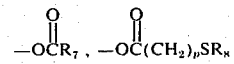

and

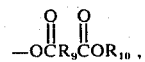

or X and Y together form a divalent radical selected from the group consisting of

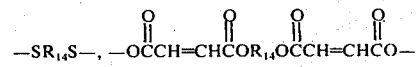

and

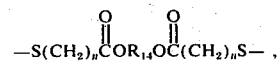

$Q_2$ represents a divalent radical of a formula selected from the group consisting of

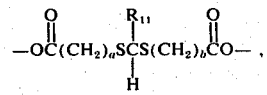

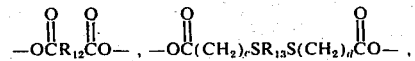

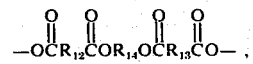

and wherein $R_3$ is an alkyl radical containing between 1 and 20 carbon atoms or a substituted or unsubstituted phenyl or alkylphenyl radical, $R_4$ is selected from the same group as $R_3$, $R_5$ is an alkyl radical containing between 1 and 20 carbon atoms, or a substituted or unsubstituted phenylalkyl radical wherein the alkyl portion of said phenylalkyl radical contains between 1 and 6 carbons atoms, $R_6$ and $R_7$ are selected from the same group as $R_3$, $R_8$ is selected from the same group as $R_5$, $R_9$ is a single bond, an alkylene radical containing between 1 and 20 carbon atoms, an alkylene radical containing between 2 and 20 carbon atoms or a substituted or unsubstituted phenylene radical, $R_{10}$ is selected from the same group as $R_4$, $R_{11}$ is selected from the same group as $R_3$, $R_{12}$ is a single bond, an alkylene radical containing between 1 and 20 carbon atoms, an alkenylene radical containing between 2 and 20 carbon atoms or a substituted or unsubstituted phenylene radical, $R_{13}$ is an alkylene radical containing between 1 and 20 carbon atoms or said alkylene radical substituted with at least one phenyl radical, an alkenylene radical containing between 2 and 20 carbon atoms, or a cycloalkylene radical containing 5 or 6 carbon atoms, $R_{14}$ is an alkylene radical containing between 1 and 20 carbon atoms, and $a$, $b$, $c$, $d$, $n$ and $p$ are each selected from the integers 1 to 6, inclusive.

16 Claims, No Drawings

NOVEL DIORGANOTIN DERIVATIVES OF α,ω-DIMERCAPTANS AND METHOD FOR PREPARING SAME

This application is a continuation-in-part of application Ser. No. 359,176, filed May 10, 1973 now abandoned.

The present invention relates to organotin compounds, processes for preparing them and to their use as stabilizers for polymeric materials in particular halogenated resins such as polymers and copolymers of vinyl and vinylidene chloride.

The use of organotin compounds containing sulphur as stabilizers for halogenated resins has for many years been recognized as being highly effective. However, the compounds employed have normally been those having a comparatively high tin content and so, in view of the high cost of tin, are expensive relative to other available stabilizers. Thus, despite their high efficiency these compounds are still not as widely used as other, less effective, materials.

The compounds of the present invention are sulphur-containing organotin compounds which have a lower tin content than most conventional sulphur-containing organotin compounds and so are potentially cheaper. The stabilizing ability of some of them may match that of some of the conventional materials and so may be able to achieve the same degree of stabilization (on an equal tin basis) for lower cost.

The present invention provides organothiotin compounds of the formula

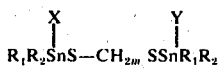

wherein $R_1$ and $R_2$ are individually selected from the group consisting of alkyl radicals containing between 1 and 20 carbon atoms, cycloalkyl and phenyl radicals, m is an integer between 1 and 8, inclusive, and X and Y are individually selected from the group of radicals exhibiting the formulae

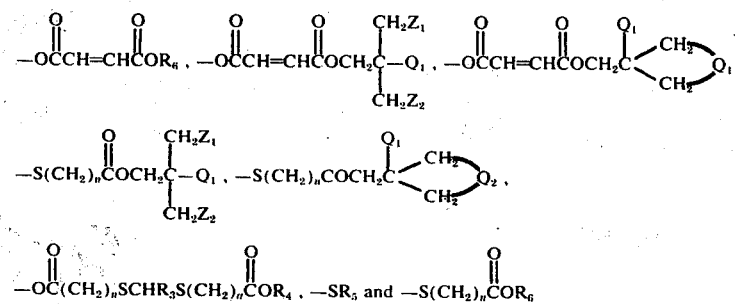

wherein $Q_1$ represents a hydrogen atom, an alkyl radical containing between 1 and 6 carbon atoms, inclusive, or the radical $CH_2Z_3$, wherein $Z_1$, $Z_2$ and $Z_3$ are individually selected from the group of radicals exhibiting the formulae

or X and Y together form a divalent radical selected from the group consisting of $-SR_{14}S-$,

$Q_2$ represents a divalent radical of a formula selected from the group consisting of

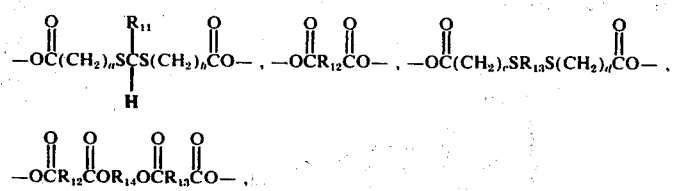

and wherein $R_3$ is an alkyl radical containing between 1 and 20 carbon atoms or a substituted or unsubstituted phenyl or alkylphenyl radical, $R_4$ is selected from the same group as $R_3$, $R_5$ is an alkyl radical containing between 1 and 20 carbon atoms, or a substituted or unsubstituted phenylalkyl radical wherein the alkyl portion of said phenylalkyl radical contains between 1 and 6 carbon atoms, $R_6$ and $R_7$ are selected from the same group as $R_3$, $R_8$ is selected from the same group as $R_5$, $R_9$ is a single bond, an alkylene radical containing between 1 and 20 carbon atoms, an alkenylene radical containing between 2 and 20 carbon atoms or a substituted or unsubstituted phenylene radical, $R_{10}$ is selected from the same group as R. $R_{11}$ is selected from the same group as $R_3$, $R_{12}$ is a single bond, an alkylene radical containing between 1 and 20 carbon atoms, an alkenylene radical containing between 2 and 20 carbon atoms or a substituted or unsubstituted phenylene radical, $R_{13}$ is an alkylene group containing between 1 and 20 carbon atoms or said alkylene radical substituted with at least one phenyl radical, an alkenylene radical containing between 2 and 20 carbon atoms, or a cycloalkylene radical containing 5 or 6 carbon atoms, $R_{14}$ is an alkylene radical containing between 1 and 20 carbon atoms, and $a, b, c, d, n$ and $p$ are each selected from the integers 1 to 6, inclusive.

Preferably the radical

is of the formula

or

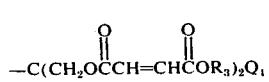

and the radical

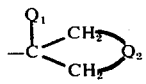

is of the formula

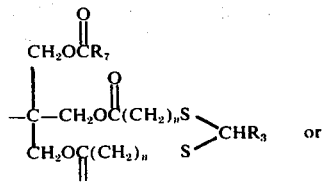   or

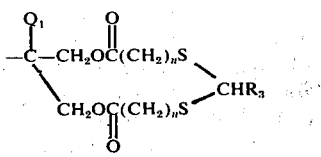

In preferred compounds of the invention, $R_1$ and $R_2$ are n-butyl or n-octyl groups, $R_3$ is an alkyl group of 8–20 carbon atoms, preferably an n-undecyl group, or a hydroxyphenyl group, preferably an o-hydroxyphenyl, $R_5$ is an alkyl group of 8–20 carbon atoms, preferably an n-dodecyl group, $R_6$ is an alkyl group of 8–20 carbon atoms, preferably an iso-octyl or 2-ethylhexyl group, each of $n$ and $a$ which are the same or different, is 1 or 2, $n$ being preferably 2 and $a$ 1, the group $C_m H_{2m}$ is linear (ie. of formula $(CH_2)_m$) and $m$ is especially 6.

Examples of particular compounds according to the present invention are:

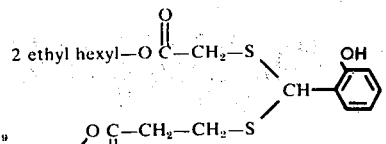

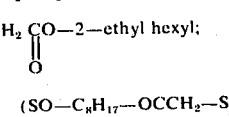

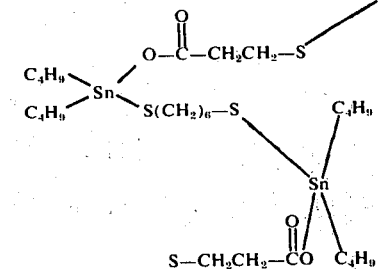

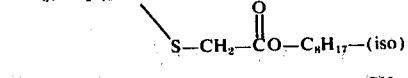

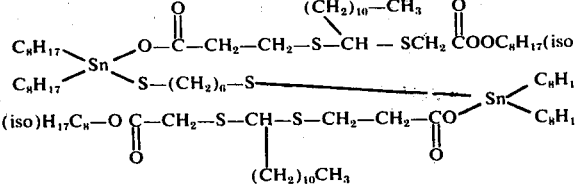

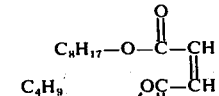

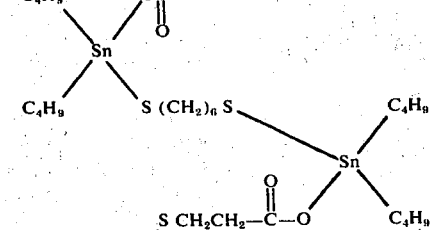

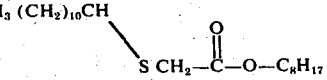

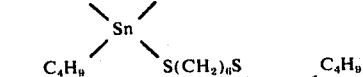

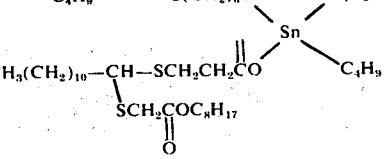

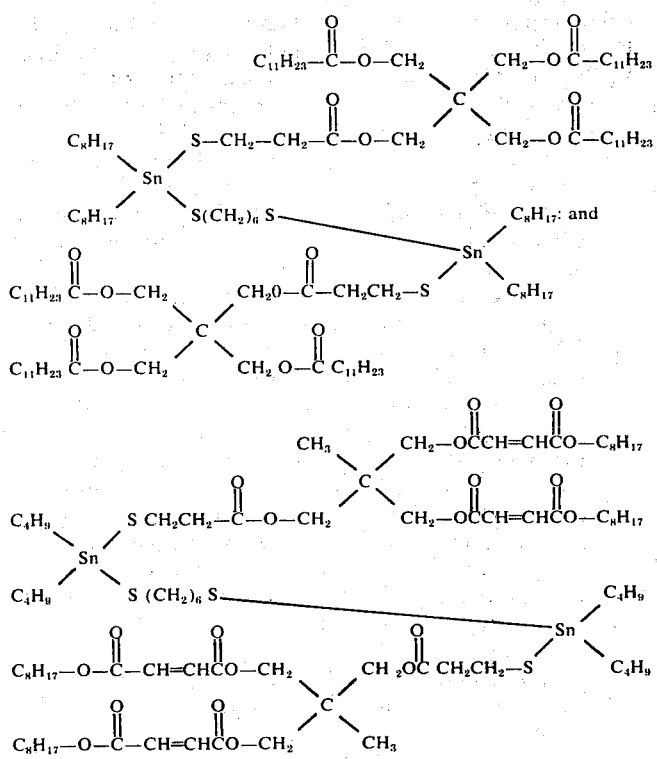

The compounds of the invention, having the structure given, are believed to be the products of the process of the invention which comprises reacting one mole of a dithiol of the formula $HSC_mH_{2m}$ for every 2 moles of reaction product of (1) a diorganotin oxide, sulfide or dihalide nd (2) an equimolar mixture of HX and HY. When X, Y, or both are represented by the formula

the reactant is the corresponding maleate half ester, mercaptan or mercaptoacid ester, respectively. When X and Y are bonded together to form a divalent radical of the formula

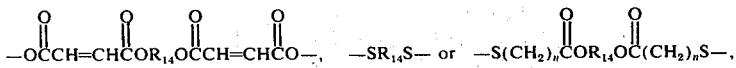

1 mole of disulfide and two moles of the diorganotin compound are reacted with one mole of the corresponding glycol maleate, disulfide, $HSR_{14}SH$, or glycol mercaptocarboxylate, respectively. Reactants HX or HY of the formula

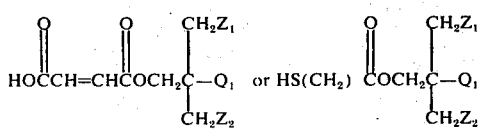

are derived from a partially esterified polyhydric alcohol,

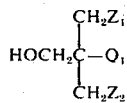

containing one free hydroxyl group and maleic acid or a mercaptocarboxylic acid. The remainig two or three hydroxyl groups are "blocked" by esterification with a monocarboxylic acid

a mercaptocarboxylic acid $HOC(CH_2)_nSR_8$ or a half ester of a dircaroxylic acid,

This class of compounds can be prepared by a process which comprises reacting the polyhydric alcohol, which is pentaerythritol or triol of the formula $(HOCH_2)CQ_1$, a mercapto acid of the formula $HS(CH_2)_nCOOH$ wherein $n$ is an integer of 1 to 6, and one or more of the aforementioned blocking agents.

If a dicarboxylic acid or certain reaction products containing two

radicals is employed to block two of the hydroxyl radicals present on the aforementioned polyhydric alcohol and the resultant portial ester is then reacted with maleic or a mercaptocarboxylic acid, the X and/or Y radical present in organotin compound will contain a $Q_2$ radical as defined hereinbefore. In addition to dicarboxylic acids, the divalent blocking agent can also be (1) the reaction product of 1 mole each of a mercaptocarboxylic acid

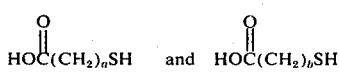

with one mole of an aldehyde

(2) the reaction product of equimolar amounts of mercaptocarboxylic acids

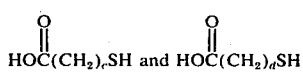

with an equimolar amount of a dihalide $XR_{13}X$, wherein X represents a halogen atom or (3) the reaction product of equimolar amounts of dicarboxylic acids

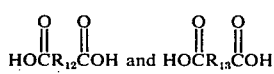

with a diol $HOR_{14}OH$. Reactants HX and HY that contain a

radical are derived from an aldehyde of the formula

and equimolar amounts of a mercaptocarboxylic acid

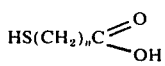

and a mercaptoester

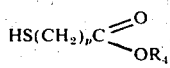

The molar ratio of aldehyde to combined ester and acid is 1:2.

Blocking agents of the formula $R_7COOH$ or $HOOCR_9COOR_{10}$ (or the component dicarboxylic acid and alcohol) are used when the number of moles of hydroxyl radicals exceeds the number of moles of mercaptoacid,

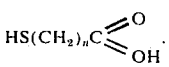

An aldehyde, organic dihalide $HalR_{12}Hal$ or mono-halide $R_8Hal$ is employed when the polyhydric alcohol is a triol and the number of moles of triol is less than the number of moles of mercaptoacid or when the polyhydric alcohol is pentaerythritol wherein the molar quantity of pentaerythritol is less than half the number of moles of mercaptoacid that is reacted with the alcohol.

The alcoholic component, mercaptoacid and blocking agent are reacted in any order to produce an intermediate containing on;lu one SH group per mole if the polyhydric alcohol is a triol, or 1 or 2 SH groups per mole if the polyhydric alcohol is pentaerythritol. The resultant intermediate is reacted with an organotin compound of formula $R_1R_2SnO$ or $R_1R_2SnHal_2$ in an amount of not more than 1 mole of organotin compound for each mole of radical derived from the pentaerythritol or triol that is present in the intermediate.

Frequently all of the reactants required to prepare the intermediate HX and HY will be mixed together and heated in a suitable solvent, such as an aromatic hydrocarbon e.g. toluene, or xylene, or other organic solvents such as hexane, petrol, or cyclohexane. Normally it will be desirable to have an acidic catalyst present such as p-toluene sulphonic acid, hydrochloric acid or metal chlorides suitable as Friedel Craft catalysts such as zinc chloride.

Compounds of the formula $R_1R_2SnX_2$, $R_1R_2SnY_2$ and $R_1R_2SnXY$ wherein at least one of X and Y is of formula

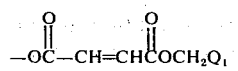

are described and claimed in our co-pending Application Ser. No. 359,177, filed May 10th 1973 now abandoned.

In place of the combination diorganotin oxide, sulfide or dihalide with HX and HY one can prereact one or both of HX and HY with a portion of the diorganotin compound, and subsequently react this intermediate with the remaining diorganotin oxide, sulfide or dihalide to obtain the final product. The various combinations of starting materials which can be reacted with the dithiol to prepare the present compounds are summarized as follows:
 a. $R_1R_2SnXY$ and $R_1R_2SnHal$
 b. $R_1R_2SnXY$ and $R_1R_2SnE$
 c. $R_1R_2SnXHal$ and $R_1R_2SnHal_2$ and HY
 d. $R_1R_2SnXHal$ and $R_1R_2SnE$ and HY
 e. $R_1R_2SNHal_2$ and HX and HY
 f. $R_1R_2SnE$ and HX and HY The radical "E" represents oxygen or sulfur.

The present organotin compounds are effective heat stabilizers for halogen-containing resins. Accordingly, the present invention also provides a composition which comprises a halogen-containing resin (as hereinafter defined) and as a stabilizer therefore at least one compound of the formula

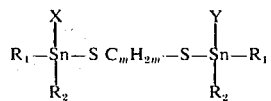

where $R_1$, $R_2$, X, Y, and $m$ are as hereinbefore defined.

In the present specification, halogen-containing resins are defined as polymers or copolymers of vinyl chloride or vinylidene chloride, chlorinated vinyl chloride polymers or chlorinated polyethylene.

The organotin compounds will be present in compositions according to the invention in amounts so as to produce the desired stabilizing effect; often this will be 0.01–10%., preferably 0.2–5%. especially 2 to 3% by weight based on the total amount of polymeric resin present.

We have also found that by admixing from 1 to 50% by weight (based on the weight of organotin compound of the invention) of a monobutyltin compound e.g. monobutyltin tri(isooctylthioglycollate) with the compounds of the invention, their stabilising efficiency may be enhanced. Other additives which may have a similar effect include monooctyltin tris (iso-octyl thioglycollate), di-butyltin sulphide, dioctyltin sulphide, di-n-butyltin cyclic-mercapto acetate, di-n-butyltin cyclic β-mercapto propionate (and their di-n-octyltn analogues).

Optionally, but advantageously, compositions according to the invention also contain at least one hindred phenol, (defined herein as ones having at least one alkyl substitutent in a position ortho to the hydroxyl group) as auxilliary stabilisers. Such phenols which are of use in compositions of the present invention include butylated hydroxyanisole, 2,6-di-tert.-butylphenol, methylene bis (2,4-di-tert.-butylphenol), methylene bis-(2,6-di-tert.-butylphenol), methylene bis-(2,6-di-tert,-butyl-3-methylphenol), 4,4'-butylidene bis-(6-tert.-butyl-3methylphenol), methylene bis- (4-ethyl-6-tert. butylphenol), and methylene bis-(4-methyl-2,6-di-tert.-butylphenol). Particularly preferred, however, is 2,6-di-tert.-butyl-4-methylphenol. Such phenols may be present in an amount of up to 3%, preferably from 0.01 to 0.05% by weight of the resin and will normally be present at aboiut 4–10% by weight, preferably 5–8%., based on the total amount of organotin compounds used.

Esters of phosphorous and thiophosphorous acid may be employed in compositions according to the invention. Such compounds include halo-phosphites such as trischloropropyl phosphite and polymeric phosphites such as those derived from hydrogenated 4,4' -isopropylidenediphenol. Preferred phosphites and thio-phosphites, however, are monomers having no substituents in the organo-group and having no more than one sulphur atom. These includes triaryl phosphites and trialkyl phosphites. Such compounds include, for example, triphenyl phosphite, trixylylphosphite, tri(nonyl phenyl) phosphite and trioctyl phosphite. Diesters of phosphorous acid such as di-isopropyl phosphite, dibutyl phosphite and diphenyl phosphite are also of use. Particlarly preferred, however, are the mixed alkyl aryl phosphites such as octyl diphenyl phosphite, isodecyl diphenyl phosphite and di-isodecyl phenyl phosphite. This particularly pronounced effect may also be obtained by employing a mixture of a triaryl phosphite and an alcohol in conjunction with the organotin compound. A particularly suitable mixture is that of triphenyl phosphite and isodecanol.

The stabiliser composition is also useful if it is employed in a polymer composition containing an epoxy compound, as may be desired for example in cases where a delay of initial colour change is desired. Epoxy compounds which may be employed in such compositions include butyl epoxy stearate, esters of epoxidised oleic acid and compounds of the formula.

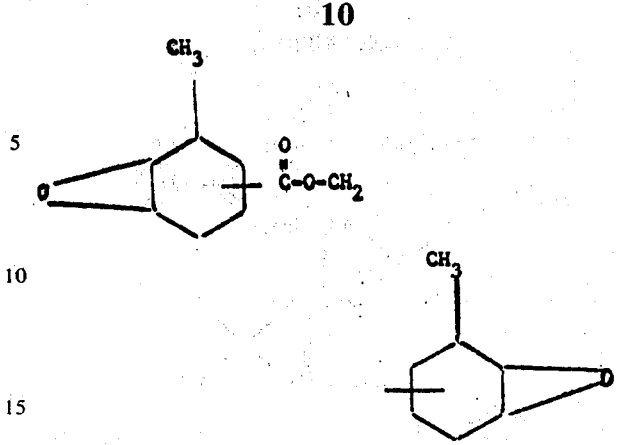

Organotin formulations as described above, optionally including a hindered phenol, an alkylaryl phosphite or aryl phosphite or an epoxide, will often be used as the only stabiliser in a polymeric vinyl chloride or vinylidene chloride composition. However, if desired conventional thermal stabilisers may also be included. These may include, for example, metal soap stabilisers, such as cadmium, barium or zinc salts of fatty acids, or lead salts such as lead carbonate or stearate or dibasic lead phosphate or phthalate, or tribasic lead sulphate or conventional organotin stabilisers such as dibutyltin dilaurate or dibutyltin maleate or sulphur-containing compounds such as dibutyltin bisthioglycollates.

In the practice of the invention the stabiliser formulation may be mixed with the copolymer resin in the conventional manner for example by milling with the resin on heated rolls at 100°–160°C, eg about 150°C, although higher temperatures may be used when convenient, or by being mixed with particles of the polymer and then melting and extruding the mixture or by adding the stabiliser to a liquid resin.

Resins may be used in compositions according to the invention normally contain at least 40% by weight of chlorine. Usually it will be a polymer or copolymer of vinyl chloride or vinylidene chloride but post-halogenated polyvinyl chloride or post-halogenated polyolefins, such as polyethylene, may be employed if desired. Suitable monomers, which may form such copolymers with vinyl chloride and vinylidene chloride, include for example acrylonitrile, vinyl acetate, methyl methacrylate, diesters of fumaric acid and maleic acid, ethylene, propylene and lauryl vinyl ether and these co-monomers may be present in an amount of up to 25% of the total weight of monomers copolymerised.

The organotin stabiliser formulation may be employed in ether plasticised resin compositions, for example those plasticised with carboxylic ester plasticisers e.g. di-2-ethyl-hexyl phthalate, dibutyl sebacate and di-isooctyl phthalate or phosphate plasticiser e.g. (alkyl aryl)phosphates or may be employed in rigid compositions. Such rigid compositions contain little or no plasticiser although for some applications up to about 10% by weight of plasticiser may be present. This is in contrast with plasticised compositions where the amount of plasticiser present is normally at least 30% e.g greater than 50% by weight of the polymeric material and is often greater than 100% on that basis eg. up to 150%.

In addition to the stabilizers, the compositions of the invention may also contain conventional additives, e.g. pigments, fillers, dye and ultraviolet absorbing agents.

The process of the invention will be illustrated by the following examples:

EXAMPLE 1

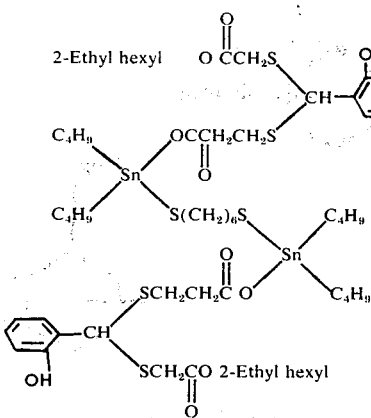

Salicylaldehyde (24.4g, 0.2M), 2 Ethyl hexyl thioglycollate (40.8g, 0.2M) and β-mercaptopropionic acid (21.2g, 0.2M) were refluxed in toluene (150 ml) in presence of p-toluene sulphonic acid (ca 0.1g) till the calculated amount of water had collected

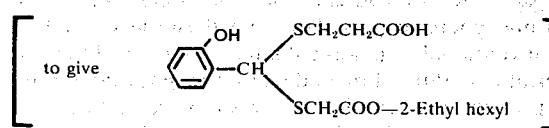

Dibutyltin oxide (24.9 g, 0.1M) was then added to the above warm solution and the mixture refluxed as above

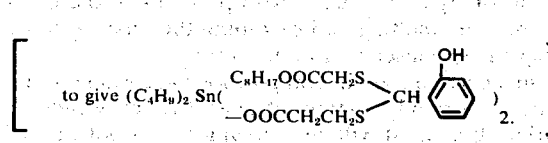

After cooling the solution additional dibutyltin oxide (24.9g, 0.1M) was added and the mixture refluxed until a clear solution was obtained. 1,6-Hexanedithiol (15.0g, 0.1M) was then added dropwise using a separatory funnel to the above warm solution and the mixture refluxed until the reaction was complete (as in Example 1). The product is a light yellow liquid.

| Analysis | |
|---|---|
| Calculated | Found |
| C = 51.7% | C = 52.65% |
| H = 7.4% | H = 7.72% |
| S = 13.3% | S = 13.6% |

The structure of the compound was confirmed by infra red (I.R.) and nuclear magnetic resonance (N.M.R.) spectra.

EXAMPLE 2

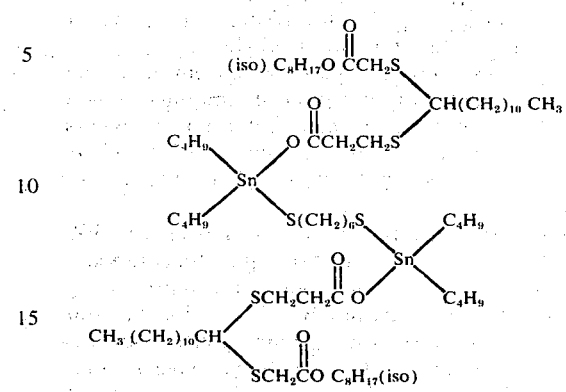

This compound was prepared by the same method as in Example 1 using the following quantities.

| Step (1) | (a) Dodecylaldehyde | 73.6g |
|---|---|---|
| | (b) β-mercaptopropionic aid | 42.4g |
| | (c) Iso-octyl thioglycollate | 81.6g |
| | (d) p-Toluene sulphonic Aid | ca0.2g |
| | (e) Toluene | 200 ml |
| step (2) | (f) Dibutyltin oxide | 49.8g |
| step (3) | (g) Dibutyltin oxide | 49.8g |
| step (4) | (h) 1,6, Hexane dithiol | 30 g |

The product is a light yellow liquid.

| Analysis | |
|---|---|
| Calculated | Found |
| Sn = 15.18% | Sn = 15.4% |
| S = 12.28% | S = 12.3% |
| C = 55.26% | C = 55.23% |
| H = 9.08% | H = 9.27% |

Product structure was also confirmed by I.R. and N.M.R. spectra.

EXAMPLE 3

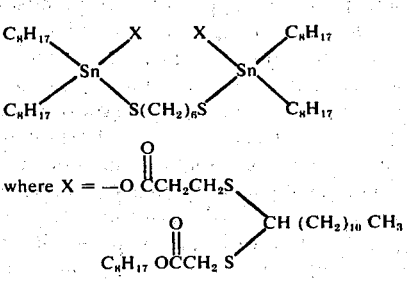

This compound was prepared by the same method as example 2 using the following starting materials

| step (1) | (a) Oc$_2$SnX$_2$ | 129.5 g |
|---|---|---|
| | (b) Oc$_2$SnO | 36.07g |
| step (2) | (c) 1,6-Hexane dithiol | 15 g |

The product is a light yellow liquid.

The compound of formula $Oc_2SnX_2$ was prepared using the same quantities of starting materials as in steps 1 and 2 of Example 2 and the same method for steps 1 and 2 but replacing dibutyltin oxide by dioctyltin oxide (72.14g).

EXAMPLE 4

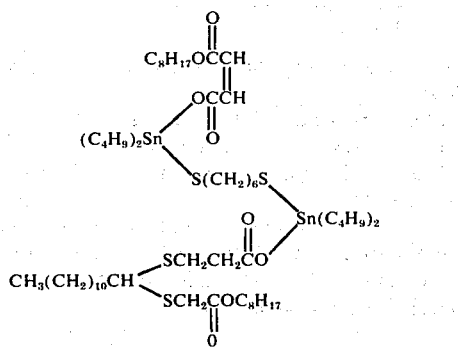

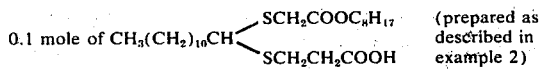

0.1 mole of $HOOCCH = CHCOOC_8H_{17}$, 0.1 mole of $CH_3(CH_2)_{10}CH\begin{smallmatrix}SCH_2COOC_8H_{17}\\SCH_2CH_2COOH\end{smallmatrix}$ (prepared as described in example 2)

and 0.1 mole of $Bu_2SnO$ were refluxed in toluene until the reaction was completed, as evidenced by formation of a clear solution. The product is a light yellow liquid.

| Analysis | |
|---|---|
| Calculated | Found |
| Sn = 12.7% | Sn = 12.7% |
| S = 6.8% | S = 7.5% |
| C = 57.7% | C = 58.1% |
| H = 9.0% | H = 8.79% |

The product structure was also confirmed by I.R. and N.M.R. spectra.

0.1 mole of this product and 0.1 mole (ie. 24.9g) of dibutyltin oxide were refluxed in toluene until a clear solution was obtained. 0.1 mole (15g) of 1,6 hexane dithiol was also added to the above solution and the mixture refluxed until the completion of the reaction. The product is a light yellow liquid.

| Analysis | |
|---|---|
| Calculated | Found |
| Sn = 18.0% | Sn = 17.5% |
| S = 9.7% | S = 10.4% |
| C = 53.8% | C = 53.6% |
| H = 8.6% | H = 8.8% |

The product structure was also confirmed by I.R. and N.M.R. spectra

EXAMPLE 5

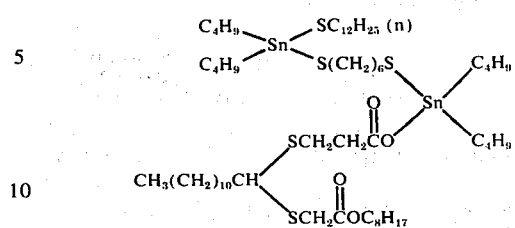

This compound was prepared by the same method as in Example 4 using the following quantities:

Step 1 (a) 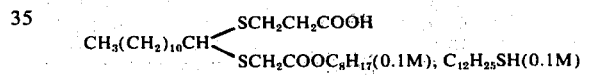

Step 2 (b) dibutyltin oxide 0.1M
Step 2 (c) 1,6 hexane dithiol 0.1M

The product is a light yellow liquid

| Analysis | |
|---|---|
| Calculated | Found |
| Sn = 18.4% | Sn = 18.5% |
| S = 12.4% | S = 12.3% |
| C = 54.9% | C = 54.6% |
| H = 9.3% | H = 9.5% |

Its structure was also confirmed by I.R. and N.M.R. analysis

The organotin compound used in step 1 (a) was prepared as follows:

$CH_3(CH_2)_{10}CH\begin{smallmatrix}SCH_2CH_2COOH\\SCH_2COOC_8H_{17}\end{smallmatrix}$(0.1M); $C_{12}H_{25}SH$(0.1M)

and $Bu_2SuO$ (0.1M) were refluxed in toluene (150 ml) until the reaction was complete. The product is a light yellow liquid.

| Analysis | |
|---|---|
| Calculated | Found |
| Sn = 13.0% | Sn = 12.9% |
| S = 10.5 | S = 11.2 |
| C = 59.4 | C = 59.5 |
| H = 9.9 | H = 9.5 |

Product structure was also confirmed by I.R. and N.M.R. spectra

EXAMPLE 6

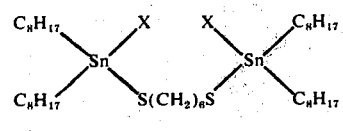

where

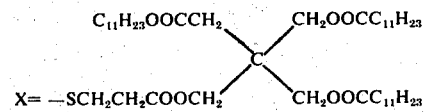

It was prepared by the same method as in Example 5 using the following quantities:

| Step (1) | (a) $(C_8H_{17})_2SnX_2$ | 37.7g (0.02M) |
|---|---|---|
|  | (b) $(C_8H_{17})_2SnO$ | 7.2g (0.02M) |
| Step (2) | (c) $HS(CH_2)_6 SH$ | 3 g (0.02M) |

The product is a white soft waxy solid at room temperature.

The compound of formula $(C_8H_{17})_2 Sn X_2$ was prepared as follows.

Pentaerythritol (27.2g, 0.2M), Lauric acid (122.4g, 0.6M) and β-mercaptopropionic acid (21.2g, 0.2M) were refluxed in toluene (200 ml) with constant stirring in the presence of p-toluene sulphonic acid (0.7g) until the calculated amount of water had collected in a Dean & Stark apparatus. Toluene was removed from the hot solution under reduced pressure, and the liquid intermediate product A $(HSCH_2CH_2COOCH_2$ -C-$(CH_2OOCC_{11}H_{23})_3$ rapidly filtered under vacuum. When stored at ambient temperature the liquid converted to a soft waxy solid.

64g (0.08M) of Intermediate product A and 14.4 g (0.04M) of dioctyltin oxide were heated together with constant stirring (without any solvent) for about 2 hours. Water was removed from the hot liquid under reduced pressure and finally the hot liquid filtered under vacuum. A white soft waxy solid was obtained upon cooling.

| Calculated |  | Found |  |
|---|---|---|---|
| Sn = | 6.3% | Sn = | 6.2% |
| S = | 3.4% | S = | 3.7% |
| C = | 66.3% | C = | 67.2% |
| H = | 10.4% | H = | 10.38% |

Product structure was also confirmed by I.R. & N.M.R. spectra.

| Analysis |  |  |  |
|---|---|---|---|
| Calculated |  | Found |  |
| Sn = | 9.9% | Sn = | 9.8% |
| S = | 5.4% | S = | 6.1% |
| C = | 63.6% | C = | 63.31% |
| H = | 10.1% | H = | 10.4% |

Its structure was also confirmed by N.M.R. analysis.

EXAMPLE 7

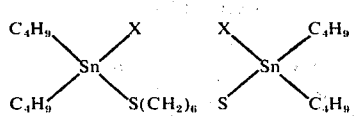

where X =

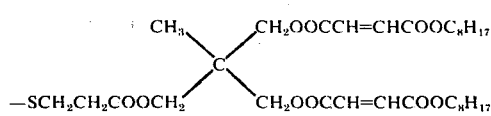

It was prepared by the same method as in Example 6 using the following quantities:

| step (1) | (a) $Bu_2SnX_2$ | = 0.1M |
|---|---|---|
|  | (b) $Bu_2SnO$ | = 0.1M |
| step (2) | (c) $HS(CH_2)_6SH$ | = 0.1M |

The product is a light yellow viscous liquid.

| Analysis |  |  |  |
|---|---|---|---|
| Calculated |  | Found |  |
| Sn = | 12.7% | Sn 32 | 12.9% |
| S = | 6.8% | S = | 7.3% |

The compound of formula $Bu_2Sn X_2$ was prepared as follows:

Maleic anhydride (19.6g, 0.2M) and iso-octyl alcohol (26g, 0.2M) were heated under reflux in toluene (200ml) for 2 hours to give product F, (HOOCCH = $CHCOOC_8H_{17}$)

(β) -mercaptopropionic acid (10.6g, 0:1M), 1,1,1 - Trimethylol ethane (11.8, 0.1M) and p-toluene sulphonic acid (0.5g) were added into the above solution (containing F) to give product G,

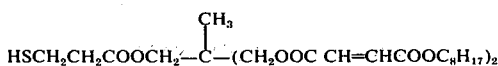

Dibutyltin oxide (12.5g, 0.05M) was then added to the solution (containing product G) and the mixture refluxed to yield the desired product. Toluene was removed from the solution as previously described, whereupon a light yellow viscous liquid was obtained.

| Analysis |  |  |  |
|---|---|---|---|
| Calculated |  | Found |  |
| Sn = | 7.9% | Sn = | 8.29% |
| S = | 4.4% | S = | 4.67% |
| C = | 58.1% | C = | 57.6% |
| H = | 8.0% | H = | 7.99% |

EXAMPLE 8

The stabilizers of the present invention can be used with halogen containing vinyl and vinylidene resins in which the halogen is attached directly to the carbon atoms of the polymer chain. Preferably, the resin is vinyl halide resin, especially a vinyl chloride, resin.

A number of compounds of the present invention were tested for initial colour development against known stabilizers on an equal tin basis and it was shown that they compared favorably (see Table 1).

The example illustrates the stabilizing effectiveness of the of the compounds of the present invention (with and without additives) in comparison with a known butyltin mercaptoester stabilizer(Mellite 31c) containing an equal amount of tin in rigid P.V.C. compositions.

A series of rigid (non-plasticized) formulation was prepared having following composition:

(a) Corvic D55/9    100 parts.
(b) Plasticube 30 Marked T if added and the amount present in part per 100 parts of polymer (phr) are indicated inside the brackets. In many instances of the present invention plastilube has not been added to the polymer due to the reason that many of the compounds tested are themselves acting as a lubricant during milling at about 155°C c. Stabilisers and additives All examples in Table 1 have been tested (with and without additives) separately in comparison with mellite 31c containing equal amount of tin in definite amount of Corvic D55/9 (usually 300 gms).

| A | represents | B.F.S. (butyl epoxy stearate) |
|---|---|---|
| L | " | M31C (Mellite 31C) |
| B | " | $BuSn(SCH_2COOC_8H_{17})_3$ |
| R | " | $OcSn(SCH_2COOC_8H_{17})_3$ |
| I | " | $Bu_2SnS$ |
| G | " | $Bu_2Sn\begin{smallmatrix}S-CH_2\\ \phantom{Bu_2Sn}\diagdown\phantom{xx}\diagup\\ \phantom{Bu_2SnS}O\phantom{xx}C-O\end{smallmatrix}$ |
| T | " | Plastilube 30 |

Table 1

| STABILIZER ( ) denotes wt. % | PARTS OF STABILIZERS PER 100 PARTS POLYMER | Colour on gardener Scale after given time in minutes at 190°C | | | | |
|---|---|---|---|---|---|---|
| | | 0 | 5 | 10 | 15 | 20 |
| Product of Ex. 1 (95) +B(5)+T(0.5) | 1.66 | 0 | 0 | 1 | 3 | |
| Product of Ex. 1 (95) +B(5)+A(20)+T(0.5) | equivalent to the above | 0 | 0 | 1 | 3 | |
| Product of Ex. 1 (95) +B(5)+L(20)+T(0.5) | " | 0 | 0 | 0 | 3 | |
| Product of Ex. 1 (95) +B(5)+L(20)+A(20)+T(0.5) | " | 0 | 0 | 0 | 2-3 | |
| Mellite 31C+T(0.5) | " | 0 | 0 | 3 | 5 | |
| Product of Ex. 2 (95) +B(5)+T(0.5) | 1.6 | 0 | 0 | 1 | 2 | |
| Product of Ex. 2 (90) +B(5)+I(5)+T(0.5) | equivalent to the above | 0 | 0 | 0–1 | 2 | |
| Product of Ex. 2 (95) B(5)+L(25)+T(0.5) | " | 0 | 0 | 0 | 2 | |
| Product of Ex. 2 (95) +B(5)+A(15)+T(0.5) | " | 0 | 0 | 1 | 2-3 | |
| Mellite 31C+T(0.5) | " | 0 | 0 | 1 | 5 | |
| Thermallite 31+T(0.5) | 2 Parts | 0 | 0–1 | 4 | 6 | |
| Product of Ex. 4 (95) +B(5) | tin equivalent to above | 0 | 0 | 0–1 | 2 | |
| Mellite 31C+T(0.5) | " | 0 | 0 | 1 | 3 | |

What is claimed is:

1. An organotin compound of the formula $$R_1R_2SnS-C_mH_{2m}-SSnR_1R_2$$
$$\phantom{R_1R_2Sn}|\phantom{S-C_mH_{2m}-SSn}|$$
$$\phantom{R_1R_2Sn}X\phantom{S-C_mH_{2m}-SSn}Y$$

wherein $R_1$ and $R_2$ are individually selected from the group consisting of alkyl groups containing between 1 and 20 carbon atoms, cycloalkyl and phenyl groups, $m$ is an integer between 1 and 8, inclusive, at least one of X and Y represents the group $$-S(CH_2)_n\overset{O}{\underset{\|}{C}}OCH_2\overset{CH_2Z_1}{\underset{CH_2Z_2}{\overset{|}{C}-Q_1}} \quad \text{or} \quad -O\overset{O}{\underset{\|}{C}}(CH_2)_nSCHR_3S(CH_2)_p\overset{O}{\underset{\|}{C}}OR_4,$$

with the proviso that when only one of X and Y represents said group, the other represents $-SR_5$ or $$-O\overset{O}{\underset{\|}{C}}CH=CH\overset{O}{\underset{\|}{C}}OR_6;$$

$Q_1$ represents an alkyl group containing between 1 and 6 carbon atoms, inclusive, or $CH_2Z_3$, wherein $Z_1$, $Z_2$ and $Z_3$ are individually selected from the group consisting of $$-O\overset{O}{\underset{\|}{C}}R_7 \quad \text{and} \quad -O\overset{O}{\underset{\|}{C}}CH=CH\overset{O}{\underset{\|}{C}}OR_8,$$

$R_3$ represents an alkyl group containing between 1 and 20 carbon atoms, inclusive, an alkylphenyl or hydroxyphenyl group, $R_4$, $R_5$, $R_6$, $R_7$ and $R_8$ are individually selected from the group consisting of alkyl groups containing between 1 and 20 carbon atoms and $n$ and $p$ are each selected from the group consisting of integers between 1 and 6, inclusive.

2. A compound according to claim 1 wherein both X and Y are of the formula $$-S(CH_2)_n COOCH_2\overset{CH_2Z_1}{\underset{CH_2Z_2}{\overset{|}{C}-Q_1}}$$

wherein $Q_1$ is an alkyl or a $CH_2Z_3$ radical and wherein $Z_1$, $Z_2$ and $Z_3$ are of the formula $$-O\overset{O}{\underset{\|}{C}}CH=CH\overset{O}{\underset{\|}{C}}OR.$$

3. A compound according to claim 2 wherein $R_1$ and $R_2$ are n-butyl or n-octyl groups, n is 1 or 2 and $C_mH_{pm}$ represents a linear hydrocarbon radical.

4. A compound according to claim 1 wherein $R_3$ is an alkyl group of 8–20 carbon atoms or a hydroxyphenyl group.

5. A compound according to claim 1 wherein $R_5$ is an alkyl group of 8–20 carbon atoms.

6. A compound according to claim 1 wherein $R_4$ is an alkyl group of 8–20 carbon atoms.

7. A compound according to claim 1 wherein $R_1$ and $R_2$ are n-butyl or n-octyl groups.

8. A compound according to claim 1 wherein each of $n$ and $p$, which are the same or different, is 1 or 2.

9. A compound according to claim 1 wherein the group —$C_mH_{2m}$— is linear.

10. An organothiotin compound according to claim 1 of the formula

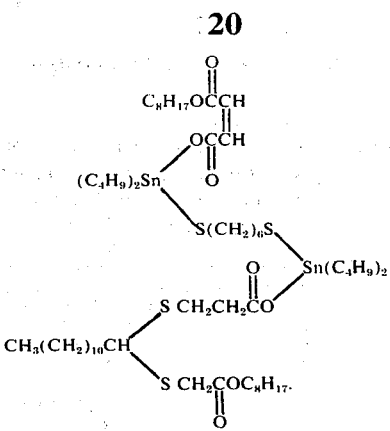

11. An organothiotin compound according to claim 1 of the formula

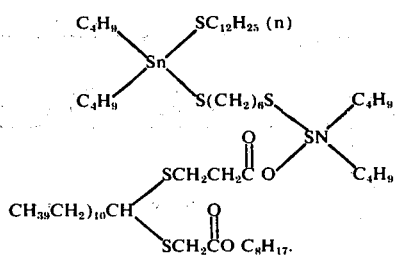

12. An organothiotin compound according to claim 1 of the formula

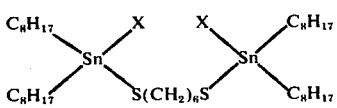

13. An organothiotin compound according to claim 1 of the formula

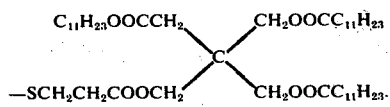

14. An organothiotin compound according to claim 1 of the formula

15. An organothiotin compound according to claim 1 of the formula

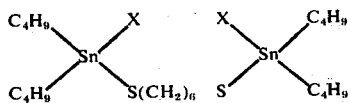

where X =

16. An organothiotin compound according to claim 1 of the formula

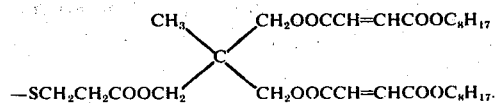

where X =

* * * * *